United States Patent
Gatayama

(10) Patent No.: US 11,194,621 B2
(45) Date of Patent: Dec. 7, 2021

(54) X-RAY COMPUTED TOMOGRAPHY APPARATUS, IMAGE GENERATION APPARATUS, AND TASK MANAGEMENT METHOD

(71) Applicant: Canon Medical Systems Corporation, Otawara (JP)

(72) Inventor: Kazuki Gatayama, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 47 days.

(21) Appl. No.: 16/356,119

(22) Filed: Mar. 18, 2019

(65) Prior Publication Data

US 2019/0286481 A1 Sep. 19, 2019

(30) Foreign Application Priority Data

Mar. 19, 2018 (JP) .............................. JP2018-051229

(51) Int. Cl.
| | | |
|---|---|---|
| *G06K 9/00* | (2006.01) | |
| *G06F 9/48* | (2006.01) | |
| *G06T 11/00* | (2006.01) | |
| *A61B 6/00* | (2006.01) | |
| *A61B 6/03* | (2006.01) | |
| *G16H 30/40* | (2018.01) | |

(52) U.S. Cl.
CPC ............ *G06F 9/4881* (2013.01); *A61B 6/032* (2013.01); *A61B 6/463* (2013.01); *G06T 11/003* (2013.01); *G16H 30/40* (2018.01); *G06T 2200/24* (2013.01)

(58) Field of Classification Search
None
See application file for complete search history.

(56) References Cited

U.S. PATENT DOCUMENTS 9,990,742 B2 * 6/2018 Park ...................... G06T 11/006
2018/0253870 A1 * 9/2018 Park .................... G06F 11/2028

FOREIGN PATENT DOCUMENTS

JP 2002-143148 5/2002

* cited by examiner

*Primary Examiner* — Wei Wen Yang
(74) *Attorney, Agent, or Firm* — Oblon, McClelland, Maier & Neustadt, L.L.P.

(57) ABSTRACT

According to one embodiment, an X-ray computed tomography apparatus includes processing circuitry. The processing circuitry generates first tasks and second tasks, for each of a plurality of reconstruction requests for image reconstruction. The processing circuitry manages an order of execution of the first tasks and the second tasks such that the second tasks are executed after the first tasks. The processing circuitry executes the first tasks and the second tasks in the managed order of execution, based on the projection data set.

20 Claims, 12 Drawing Sheets

| PRIORITY | ID | NAME | IMAGING | CONDITION | NUMBER OF IMAGES | STATUS |
|---|---|---|---|---|---|---|
| 1 | 123456 | Taro | Helical | Lung(reference) | 3/5 | Active··· |
| 2 | 123456 | Taro | Helical | Soft Tissue(reference) | 0/5 | Waiting |
| 3 | 123456 | Taro | Helical | Liver(reference) | 0/5 | Waiting |
| 4 | 123456 | Taro | Helical | Cardiac(reference) | 0/5 | Waiting |
| 5 | 123456 | Taro | Helical | Lung | 0/635 | Waiting |
| 6 | 123456 | Taro | Helical | Soft Tissue | 0/635 | Waiting |
| 7 | 123456 | Taro | Helical | Liver | 0/275 | Waiting |
| 8 | 123456 | Taro | Helical | Cardiac | 0/355 | Waiting |
| 9 | | | | | | |
| ... | | | | | | |
F I G. 4
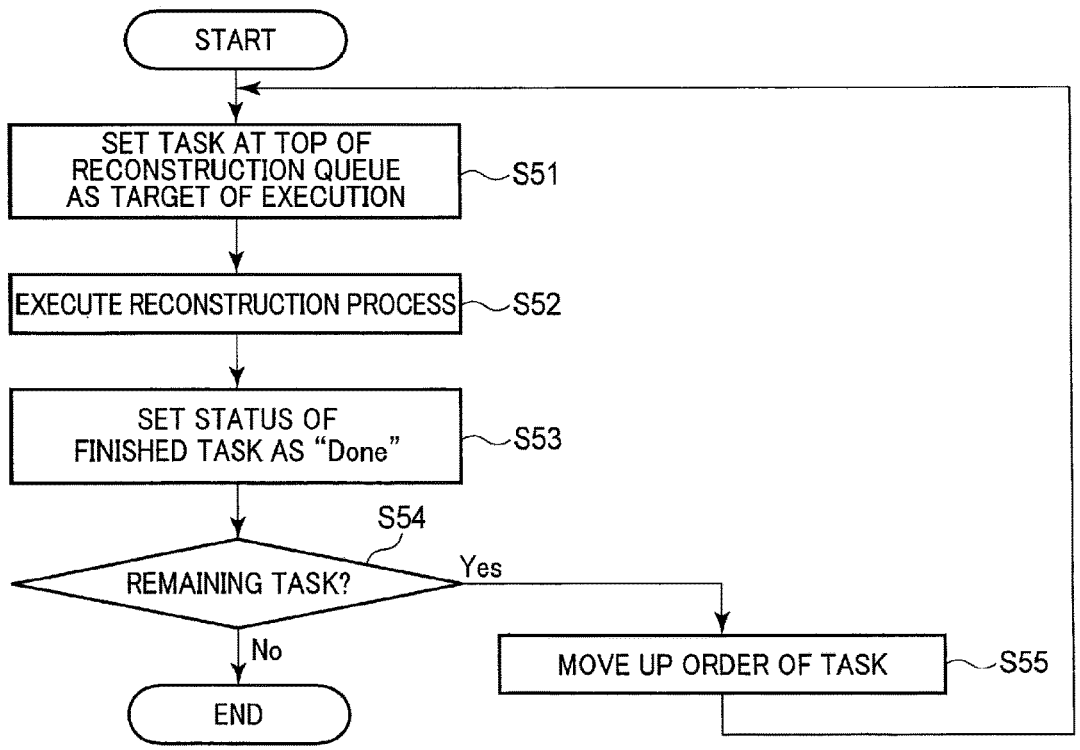
F I G. 5

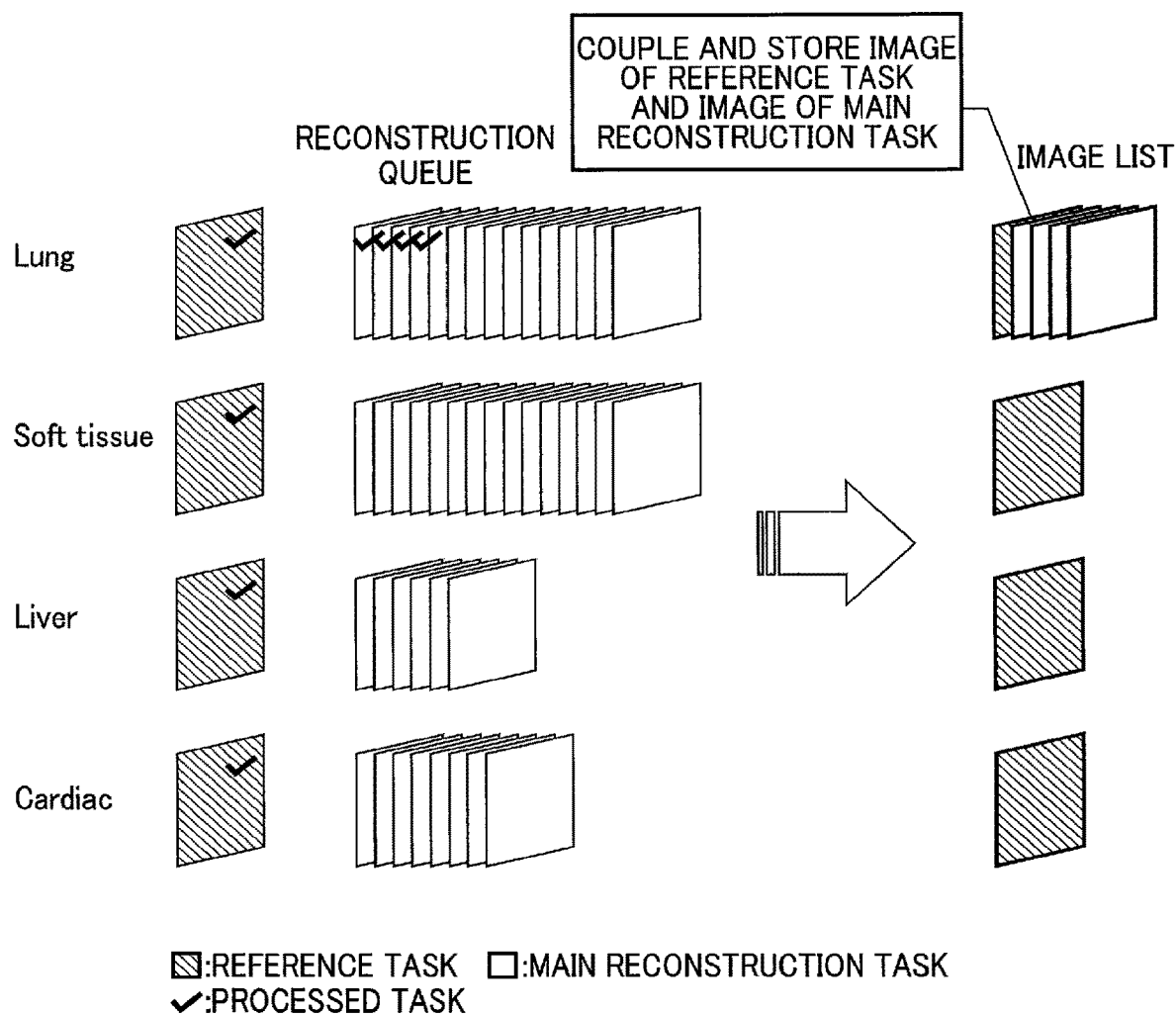
F I G. 6

Lung

Soft Tissue

Liver

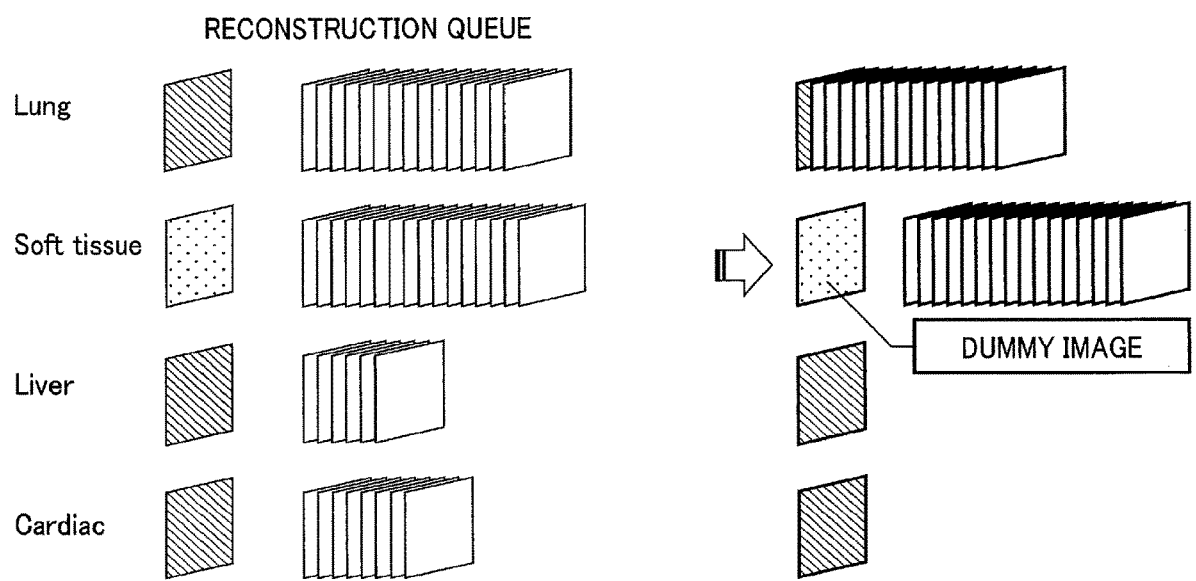
F I G. 15

X-RAY COMPUTED TOMOGRAPHY APPARATUS, IMAGE GENERATION APPARATUS, AND TASK MANAGEMENT METHOD

CROSS-REFERENCE TO RELATED APPLICATIONS

This application is based upon and claims the benefit of priority from prior Japanese Patent Application No. 2018-051229, filed Mar. 19, 2018, the entire contents of which are incorporated herein by reference.

FIELD

Embodiments described herein relate generally to an X-ray computed tomography apparatus, an image generation apparatus, and a task management method.

BACKGROUND

When the execution of an image reconstruction process was requested many times, reconstruction tasks relating to the image reconstruction process are added to a queue of reconstruction. In a conventional system, reconstruction tasks added to the queue are successively executed in the order of addition. For example, when one reconstruction task was added and then a different reconstruction task was added, the latter added reconstruction task is not executed until reconstruction images, the number of which is set in the former reconstruction task, are generated. Thus, when a user wishes to confirm reconstruction images, which are to be generated by the latter added reconstruction task, before the former reconstruction task is completed, the user needs to open a queue list of reconstruction and to change the order and priority of arranged reconstruction tasks.

As described above, in the conventional system, although it is possible to confirm, from the queue list, the reconstruction task that is in the wait state, it is not possible to confirm whether a reconstruction condition that is set for the reconstruction task is proper or not, until the reconstruction task is executed and reconstruction images are actually output. Therefore, it is time-consuming to confirm whether all images required in an examination are queued or not, and to make a survey of the entirety of the examination.

BRIEF DESCRIPTION OF THE DRAWINGS

FIG. 4 is a view illustrating a queue list which is managed by a queue management function shown in FIG. 1.

FIG. 5 is a flowchart illustrating a process at a time when the processing circuitry shown in FIG. 1 executes the reconstruction task added to the reconstruction queue.

FIG. 6 is a view illustrating main reconstruction tasks which are executed by the processing circuitry shown in FIG. 1.

FIG. 15 is a view illustrating a process in which the processing circuitry shown in FIG. 1 adds a dummy image to an image list.

DETAILED DESCRIPTION

In general, according to one embodiment, an X-ray computed tomography apparatus includes processing circuitry. The processing circuitry generates a first task corresponding to a reconstruction process of a first reconstruction range and a second task corresponding to a reconstruction process of a second reconstruction range including at least a range different from the first reconstruction range, based on a single reconstruction request for image reconstruction using a projection data set acquired by a scan including radiation and detection of X-rays. The processing circuitry manages an order of execution of the first task and the second task such that the second task is executed after the first task. The processing circuitry executes the first task and the second task in the managed order of execution, based on the projection data set. The processing circuitry generates the first task and the second task for each of a plurality of reconstruction requests. The processing circuitry manages the order of execution of a plurality of the first tasks and a plurality of the second tasks such that the second tasks are executed after the first tasks.

Hereinafter, embodiments will be described with reference to the accompanying drawings.

First Embodiment

Figure 1:
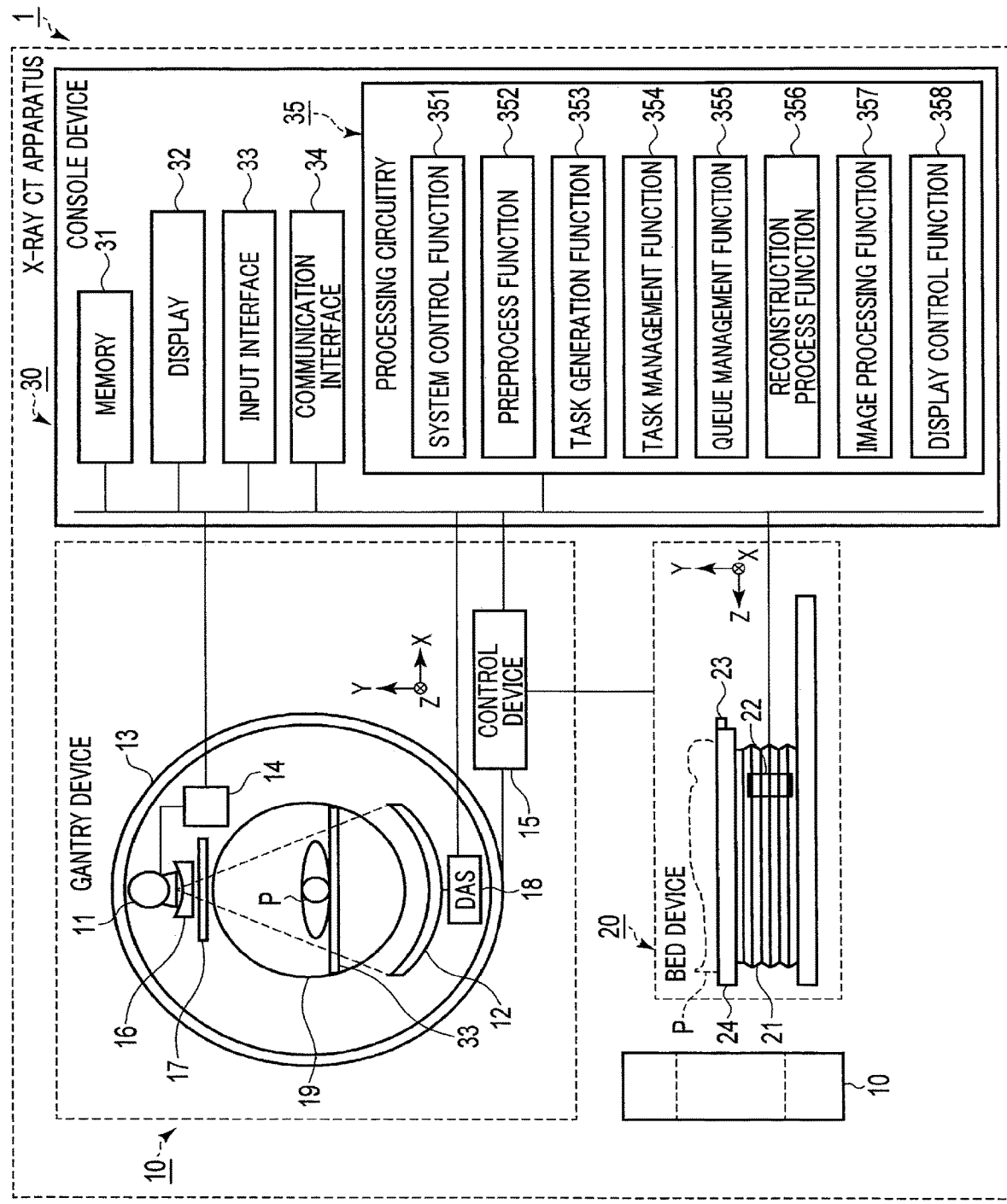
FIG. 1 is a view illustrating a configuration of an X-ray CT apparatus according to a first embodiment.

FIG. 1 is a view illustrating a configuration example of an X-ray CT apparatus 1 according to a first embodiment. In the first embodiment, the rotational axis of a rotating frame 13 in a non-tilt state or the longitudinal direction of a top 23 of a bed device 20 is defined as a Z-axis direction; an axial direction orthogonal to the Z-axis direction and horizontal to the floor surface is defined as an X-axis direction; and an axial direction orthogonal to the Z-axis direction and perpendicular to the floor surface is defined as a Y-axis direction. The X-ray CT apparatus 1 illustrated in FIG. 1 includes a gantry device 10, a bed device 20, and a console device 30. Although FIG. 1 illustrates a single-source X-ray CT apparatus by way of example, the embodiment is not limited to this. The X-ray CT apparatus according to the first embodiment may be a so-called multi-source X-ray CT apparatus in which a plurality of pairs of X-ray tubes and detectors are mounted on a rotating frame.

The gantry device 10 is a device which acquires X-ray detection data by radiating X-rays on a subject P. The gantry device 10 includes an X-ray tube 11, an X-ray detector 12, the rotating frame 13, an X-ray high voltage device 14, a control device 15, a wedge 16, a collimator 17, and a data acquisition device (DAS: Data Acquisition System) 18.

The X-ray tube 11 is a vacuum tube which radiates thermions from a cathode (filament) toward an anode (target) by a high voltage which is applied from the X-ray high voltage device 14. By the thermions being radiated from the cathode toward the anode, X-rays are generated in the X-ray tube 11.

The X-ray detector 12 detects X-rays which are generated by the X-ray tube 11, are adjusted by the wedge 16 and collimator 17, and pass through the subject P. The X-ray detector 12 outputs to the data acquisition device 18 an electric signal corresponding to the dose of the detected X-rays.

The X-ray detector 12 includes a plurality of X-ray detection element arrays, each including a plurality of X-ray detection elements arranged in a channel direction along an arc around the focal point of the X-ray tube as the center. The X-ray detector 12 is configured such that the X-ray detection element arrays are arranged, for example, in a slice direction (column direction, row direction).

In addition, the X-ray detector 12 is an indirect-conversion-type detector including a grid, a scintillator array and an optical sensor array. The scintillator array includes a plurality of scintillators, and each scintillator includes a scintillator crystal which outputs light of a photon amount corresponding to an incident X-ray dose. The grid includes an X-ray shield plate which is disposed on the X-ray incident surface side of the scintillator array, and has a function of absorbing scattered X-rays. The optical sensor array includes an optical sensor, such as a photomultiplier tube (PMT), which converts the light generated by the scintillator to an electric signal corresponding to the amount of light from the scintillator.

Note that the X-ray detector 12 may be a direct-conversion-type detector including a semiconductor device which converts incident X-rays to an electric signal.

The rotating frame 13 is an annular frame which supports the X-ray tube 11 and X-ray detector 12 such that the X-ray tube 11 and X-ray detector 12 are mutually opposed, and rotates the X-ray tube 11 and X-ray detector 12 in accordance with control from the control device 15 (to be described later). The rotating frame 13 further supports the X-ray high voltage device 14 and data acquisition device 18, in addition to the X-ray tube 11 and X-ray detector 12. Detection data generated by the data acquisition device 18 is transmitted by optical communication from a transmitter, which is provided on the rotating frame 13 and includes a light-emitting diode, to a receiver which is provided on a non-rotational portion of the gantry device 10 and includes a photodiode. The non-rotational portion of the gantry device 10 is, for example, a stationary frame (not shown) which rotatably supports the rotating frame 13. The detection data is transferred from the receiver to the console device 30. Note that the transmission method of the detection data from the rotating frame 13 to the non-rotational portion of the gantry device 10 is not limited to the optical communication. Any method may be adopted if the method performs non-contact-type data transmission.

The X-ray high voltage device 14 includes a high voltage generation device and an X-ray control device. The high voltage generation device includes electric circuitry such as a transformer and a rectifier, and has a function of generating a high voltage which is applied to the X-ray tube 11. The method in which the high voltage generation device generates the high voltage may be a transformer method or an inverter method. The X-ray control device controls the high voltage generation device so as to supply a voltage corresponding to X-rays which the X-ray tube 11 generates. The X-ray high voltage device 14 may be provided in the rotating frame 13, or may be provided in the stationary frame side of the gantry 10.

The control device 15 includes a processor which controls the operations of the gantry device 10 and bed device 20, and driving mechanisms such as a motor and an actuator. The control device 15 receives an input signal from an input interface 33 which is provided in the console device 30, and controls the operations of the gantry device 10 and bed device 20. For example, the control device 15 executes, in accordance with the input signal, control to rotate the rotating frame 13 of the gantry device 10, and control to operate the bed device 20. In addition, upon receiving an input signal from an input interface which is provided in the gantry device 10, the control device 15 controls the operation of the gantry device 10. For example, the control device 15 executes control to tilt the gantry device 10 by rotating the rotating frame 13 about an axis parallel to the X-axis direction, in accordance with inclination angle (tilt angle) information which is input from the input interface provided in the gantry device 10. The control device 15 may be provided in the gantry device 10, or may be provided in the console device 30.

The wedge 16 is a filter for adjusting the dose of X-rays which are radiated from the X-ray tube 11. Specifically, the wedge 16 is a filter which attenuates X-rays radiated from the X-ray tube 11 by passing the X-rays therethrough, such that the X-rays radiated on the subject P from the X-ray tube 11 may have a predetermined distribution. For example, the wedge 16 (a wedge filter, a bow-tie filter) is a filter formed by processing aluminum so as to have a predetermined target angle and a predetermined thickness.

The collimator 17 is lead plates or the like for restricting the range of radiation of X-rays which have passed through the wedge 16. The collimator 17 forms a slit by a combination of the lead plates or the like.

The data acquisition device 18 includes an amplifier which executes an amplification process on an electric signal which is output from each X-ray detection element provided in the X-ray detector 12, and an A/D converter which converts the electric signal to a digital signal, and the data acquisition device 18 generates detection data. The detection data which the data acquisition device 18 generates is transferred to the console device 30 via the rotating frame 13.

The bed device 20 is a device on which the subject P that is a scan target is placed, and which moves the subject P. The bed device 20 includes a base 21, a bed driving device 22, a top 23 and a support frame 24. The base 21 is a housing which supports the support frame 24 such that the support frame 24 is movable in the vertical direction. The bed driving device 22 is a motor or actuator which moves the top 23, on which the subject P is placed, in the longitudinal direction of the top 23. The top 23 is a plate on which the subject P is placed, and is provided on the top surface of the support frame 24. Note that the bed driving device 22 may move the support frame 24, in addition to the top 23, in the longitudinal direction of the top 23.

The console device 30 is a device which accepts an operation of the X-ray CT device 1 by the user, and reconstructs reconstruction image data from the detection data acquired by the gantry device 10. As illustrated in FIG. 1, the console device 30 includes a memory 31, a display 32, an input interface 33, a communication interface 34 and processing circuitry 35.

The memory 31 is realized by, for example, a semiconductor memory device such as a RAM (Random Access Memory) or a flash memory, a hard disk, an optical disc, etc. The memory 31 stores, for example, programs for the control device 15 to realize its functions, and programs for the processing circuitry 35 to realize its functions.

Further, the memory 31 stores, for example, a scan condition at a time of acquiring detection data, a reconstruction condition at a time of reconstructing reconstruction image data, and an image processing condition at a time of applying an image process to the reconstruction image data. Besides, the memory 31 stores, for example, projection data which is obtained by executing a preprocess on the detection data, reproduction image data which is obtained by executing a reconstruction process on the projection data, and medical image data which is obtained by executing an image process on the reconstruction image data.

The display 32 is an example of an output interface which outputs various kinds of information. For example, the display 32 displays, based on an instruction from the processing circuitry 35, a medical image based on the medical image data, and a GUI (Graphical User Interface) for accepting various operations from the user. Examples of the display 32 include a liquid crystal display, a CRT (Cathode Ray Tube) display, an organic EL display, an LED display, and a plasma display.

The input interface 33 accepts various input operations from the user, converts the accepted input operations to electric signals, and outputs the electric signals to the processing circuitry 35. For example, the input interface 33 accepts, from the user, a scan condition, a reconstruction condition and an image processing condition. The input interface 33 is realized by, for example, a mouse, a keyboard, a trackball, a switch, a button, and a joystick.

The communication interface 34 is connected to, for example, an intra-hospital network. The communication interface 34 transmits/receives, for example, projection data and reconstruction image data to/from an image storage device via the intra-hospital network.

The processing circuitry 35 is a processor which controls the operation of the entirety of the X-ray CT apparatus 1. The processing circuitry 35 executes a program stored in the memory 31, thereby realizing the function corresponding to the executed program. For example, the processing circuitry 35 executes a system control function 351, a preprocess function 352, a task generation function 353, a task management function 354, a queue management function 355, a reconstruction process function 356, an image processing function 357, and a display control function 358.

The system control function 351 is a function of controlling the X-ray CT apparatus 1 in order to execute scans. At this time, the processing circuitry 35 controls the X-ray CT apparatus 1, for example, based on the scan condition which is input by the input interface 33. The scan condition is set, for example, on a scan-by-scan basis, and includes information relating to a tube voltage, a tube current, and an X-ray irradiation time. When the scan condition is set, for example, the reconstruction condition is also set. The reconstruction condition includes, for example, information relating to the kind of reconstruction function, the ON/OFF of filtering, the slice thickness, reconstruction intervals, a reconstruction range, the size of a display FOV (field of view), the central position of the display FOV, and the number of images which is derived from the set values of these items and the scan range. The set scan condition and reconstruction condition are stored in the memory 31.

The preprocess function 352 is a function of correcting the detection data generated by the data acquisition device 18. Examples of this correction include a logarithmic conversion process, an offset correction process, an inter-channel sensitivity correction process, and a beam hardening correction process. In the present embodiment, the detection data, which was preprocessed, is referred to as "projection data".

The task generation function 353 is a function of generating a reconstruction task. In the present embodiment, the reconstruction task represents a reconstruction process corresponding to each of requests. The processing circuitry 35 executes the task generation function 353, for example, when the projection data is generated by the preprocess function 352 and a reconstruction process is requested by the user via the input interface 33. In the task generation function 353, the processing circuitry 35 generates the reconstruction task, based on the set reconstruction condition, etc. The processing circuitry 35 stores in the memory 31 the information relating to the generated reconstruction task.

The task management function 354 is a function of generating a reference task and a main reconstruction task, based on the reconstruction task. In the present embodiment, the reference task is a first task, which represents a reconstruction process of a small range at a freely selected position, among reconstruction processes which are executed by the reconstruction task. On the other hand, the main reconstruction task is a second task, which represents reconstruction processes excluding a reconstruction process executed by the reference task, among the reconstruction processes which are executed by the reconstruction task. The processing circuitry 35 executes the task management function 354, for example, when a reconstruction task is generated by the task generation function 353. In the task management function 354, the processing circuitry 35 refers to the reconstruction condition stored in the memory 31, and generates the reference task and main reconstruction task, based on the generated reconstruction task. For example, the processing circuitry 35 generates the reference task by rewriting the reconstruction range of the reconstruction condition of the reconstruction task to a predetermined small range. In addition, the processing circuitry 35 generates the main reconstruction task by rewriting the reconstruction range of the reconstruction condition of the reconstruction task to a range excluding the reconstruction range that was set in the reference task. The processing circuitry 35 adds, to the reference task and main reconstruction task generated based on the same reconstruction task, identification information which identifies that the reference task and main reconstruction task were generated from the same reconstruction task, thereby mutually associating the reference task and main reconstruction task. The priority of the reference task is set to be higher than the priority of the main reconstruction task. In other words, the reference task is executed with priority over the main reconstruction task. The processing circuitry 35 stores the reconstruction condition and the identification information in the memory 31 as the information relating to the reference task and the information relating to the main reconstruction task.

The queue management function 355 is a function of determining the order of execution of requested reconstruction tasks, based on the order of occurrence of requests and the priorities of the requests. The processing circuitry 35 executes the queue management function 355, for example, when the reference task and main reconstruction task are generated. In the queue management function 355, the processing circuitry 35 updates a reconstruction queue (wait queue), and adds the generated reference task and main reconstruction task to the reconstruction queue. At this time, the reference task is added to the last of reference tasks included in the reconstruction queue, and the main reconstruction task is added to the last of main reconstruction tasks included in the reconstruction queue.

In addition, in the queue management function 355, the processing circuitry 35 successively executes the tasks in the reconstruction queue from the first task. The processing circuitry 35 sets the status of the executed reference task and main reconstruction task as "processed (done)".

The reconstruction process function 356 is a function of executing a requested reconstruction task on the projection data generated by the preprocess function 352. The processing circuitry 35 executes the reconstruction tasks in the order which is managed by the queue management function 355. For example, using a filtered back projection method, an iterative approximation reconstruction method, etc., the processing circuitry 35 generates CT image data, based on the projection data.

The image processing function 357 is a function of generating medical image data in a mode desired by the user, based on the reconstruction image data generated by the reconstruction process function 356, in accordance with an input operation accepted from the user via the input interface 33. For example, by a publicly known method, the processing circuitry 35 converts the CT image data to tomographic data of a freely selected cross section and three-dimensional image data.

The display control function 358 is a function of controlling the display 32 so as to display images based on the medical image data generated by the image processing function 357.

Figure 2:
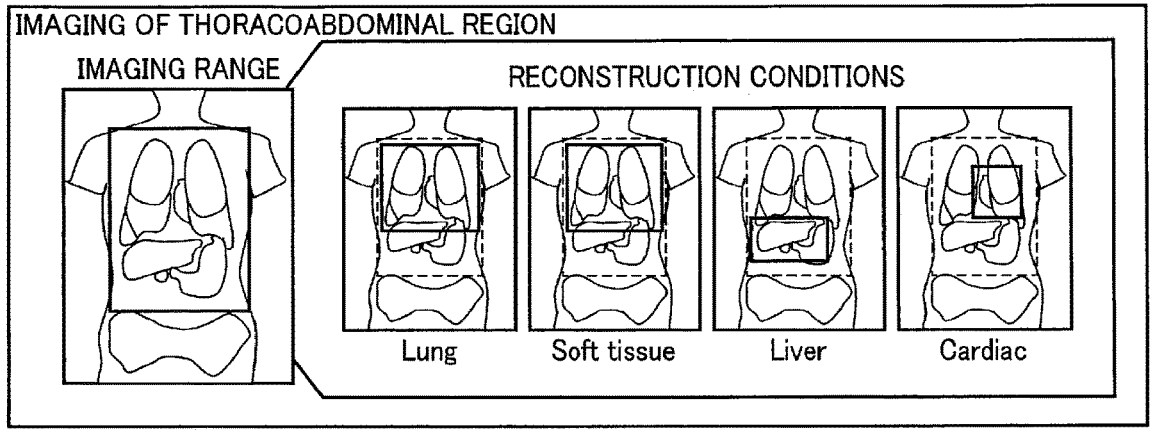
FIG. 2 is a view illustrating an example of a reconstruction process which is requested.

Next, the processes of the task generation function 353, task management function 354, queue management function 355 and reconstruction process function 356 in the X-ray CT apparatus 1 having the above-described configuration will concretely be described. In the description below, as illustrated in FIG. 2, by way of example, the case is described in which an examination of the thoracoabdominal region is performed by the X-ray CT apparatus 1, and requests are input for acquiring reconstruction images of the lungs (Lung), a soft tissue (Soft tissue), the liver (Liver) and the heart (Cardiac).

Figure 3:
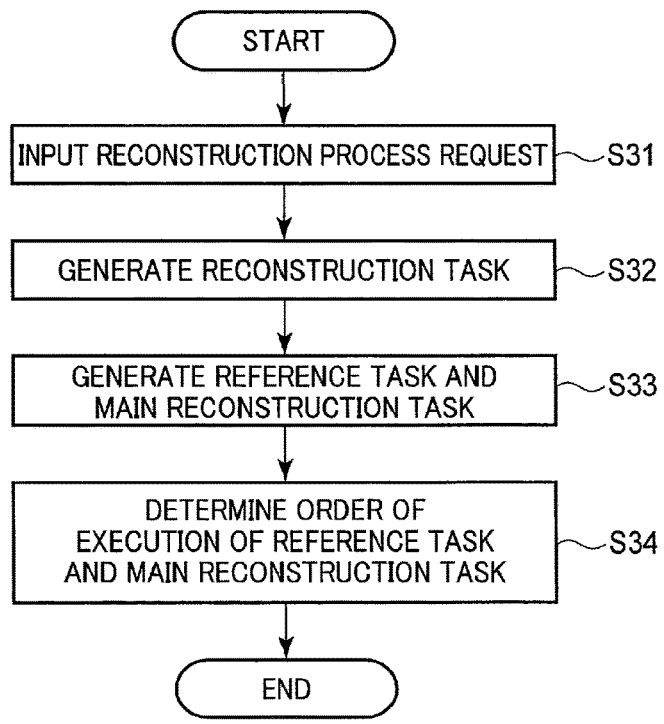
FIG. 3 is a flowchart illustrating a process at a time when processing circuitry shown in FIG. 1 adds a reconstruction task to a reconstruction queue.

FIG. 3 is a flowchart illustrating an example of a process at a time when the processing circuitry shown in FIG. 1 adds a reconstruction task to a reconstruction queue.

To start with, if the imaging of the thoracoabdominal region is completed, a request for the reconstruction process is input by the user via the input interface 33 (step S31). If the request for the reconstruction process is input, the processing circuitry 35 executes the task generation function 353. In the task generation function 353, the processing circuitry 35 reads the reconstruction condition associated with the scan from the memory 31, and generates reconstruction tasks according to the reconstruction condition (step S32). For example, in accordance with the reconstruction condition, a reconstruction task of the lungs, a reconstruction task of the soft tissue, a reconstruction task of the liver and a reconstruction task of the heart are generated, for example, in the named order.

If the reconstruction tasks are generated, the processing circuitry 35 executes the task management function 354. In the task management function 354, the processing circuitry 35 generates a reference task and a main reconstruction task, based on the requested reconstruction task (step S33). Specifically, if the reconstruction task of the lungs is generated in step S32, the processing circuitry 35 reads the reconstruction conditions relating to the reconstruction task of the lungs from the memory 31. The processing circuitry 35 rewrites a part of the reconstruction conditions, for example, the reconstruction range, and generates the reference task of the lungs and the main reconstruction task of the lungs. For example, the reconstruction range in the reconstruction condition of the lungs is written to several mm from the beginning of this range or to several mm from the position where the lungs are included, thereby generating the reference task of the lungs. In addition, the reconstruction range in the reconstruction condition of the lungs is written to a range excluding the reconstruction range set in the reference task, thereby generating the main reconstruction task of the lungs. Further, the processing circuitry 35 associates the generated reference task of the lungs and the generated main reconstruction task of the lungs, by adding identification information thereto.

In the task management function 354, the processing circuitry 35 generates reference tasks and main reconstruction tasks, based on the reconstruction task of the soft tissue, the reconstruction task of the liver and the reconstruction task of the heart, which are generated following the reconstruction task of the lungs.

If the reference tasks and main reconstruction tasks are generated, the processing circuitry 35 executes the queue management function 355. In the queue management function 355, the processing circuitry 35 determines the order of execution of the reference tasks and main reconstruction tasks, based on the order of generation of the reference tasks and main reconstruction tasks and the difference in priority between the reference tasks and main reconstruction tasks (step S34). Specifically, if the reference task of the lungs and the main reconstruction task of the lungs are generated, the processing circuitry 35 updates the reconstruction queue, adds the reference task of the lungs to the top of the reconstruction queue, and adds the reconstruction task of the lungs after the reference task of the lungs. Subsequently, if the reference tasks and main reconstruction tasks of the soft tissue, liver and heart are generated, the processing circuitry 35 adds the reference tasks of the soft tissue, liver and heart in the named order, after the reference task of the lungs. Then, the processing circuitry 35 adds the main reconstruction tasks of the soft tissue, liver and heart in the named order, after the main reconstruction task of the lungs.

FIG. 4 is a view illustrating an example of a queue list which is managed by the queue management function 355 shown in FIG. 1. According to FIG. 4, the reference tasks and main reconstruction tasks of the lungs, soft tissue, liver and heart are arranged according to the order of generation of requests and the priorities of the tasks. According to FIG. 4, the reference task of the lungs, which is arranged at the top of the reconstruction queue, is being executed (Active).

FIG. 5 is a flowchart illustrating an example of a process at a time when the processing circuitry shown in FIG. 1 executes the reconstruction task added to the reconstruction queue.

By the queue management function 355, the processing circuitry 35 sets the reference task or main reconstruction task, which is arranged at the top of the reconstruction queue, as the target of execution (step S51). By the reconstruction process function 356, the processing circuitry 35 reads out from the memory 31 the information relating to the reference task or main reconstruction task, which is the target of execution, and executes the reconstruction process on the projection data according to the read-out reconstruction condition (step S52).

According to FIG. 4, the reference task of the lungs, which is arranged at the top of the reconstruction queue, is first executed. By the execution of the reference task of the lungs, reconstruction image data is successively generated, and the generated reconstruction image data is successively added to the image list as reconstruction images by the display control function 358. If the number of images derived based on the reconstruction condition, which is five according to FIG. 4, is reached, the reference task of the lungs is finished.

If the reconstruction process is finished, the processing circuitry 35 sets, by the queue management function 355, the status of the finished reference task or main reconstruction task to be "processed" ("Done") (step S53). According to FIG. 4, the status of the reference task of the lungs, which has been processed, is set to be "Done".

Subsequently, by the queue management function 355, the processing circuitry 35 confirms whether a reference task or main reconstruction task remains in the reconstruction queue (step S54). When there remains a reference task or main reconstruction task, (Yes in step S54), the processing circuitry 35 moves up, by one, the order of the remaining reference task or main reconstruction task (step S55). Then, the processing circuitry 35 repeats the process from step S51.

According to FIG. 4, the reference task of the soft tissue, which is arranged in the second place in the order, is moved up to the first place. Then, the reconstruction process is executed by setting the reference task of the soft tissue as the target of execution.

By the reference tasks of the soft tissue, liver and heart being executed, the reconstruction image data corresponding to the respective reference tasks is successively generated. Then, the generated reconstruction image data is successively added to the image list as reconstruction images by the display control function 358.

If the reference tasks of the soft tissue, liver and heart are finished, the main reconstruction task of the lungs is then executed. By the execution of the main reconstruction task of the lungs, reconstruction image data is successively generated. The generated reconstruction image data is successively added, by the display control function 358, as reconstruction images to the image list in which reconstruction images generated by the associated reference task are managed. At this time, for example, between the reconstruction image data generated by the main reconstruction task and the reconstruction image data generated by the reference task, there is no difference due to the tasks by which the reconstruction image data was generated. Specifically, the reconstruction image generated by the main reconstruction task becomes an integral image to the reconstruction image generated by the reference task. FIG. 6 is a view illustrating an example of the main reconstruction tasks which are executed by the processing circuitry 35 shown in FIG. 1. According to FIG. 6, the reconstruction image generated during the main reconstruction task processing is coupled, at each time, to a series of previously generated reconstruction images. As regards the reconstruction image series, successive turn-over display, creation of MPR, etc. are possible. The main reconstruction task of the lungs ends when the number of images, which is derived based on the reconstruction condition and is 635 according to FIG. 4, is reached.

The processing circuitry 35 repeats the process illustrated in FIG. 5 until there remains no reference task or main reconstruction task in the reconstruction queue. When there remains no reference task or main reconstruction task in the reconstruction queue (No in step S54), the processing circuitry 35 terminates the process.

Figure 7:
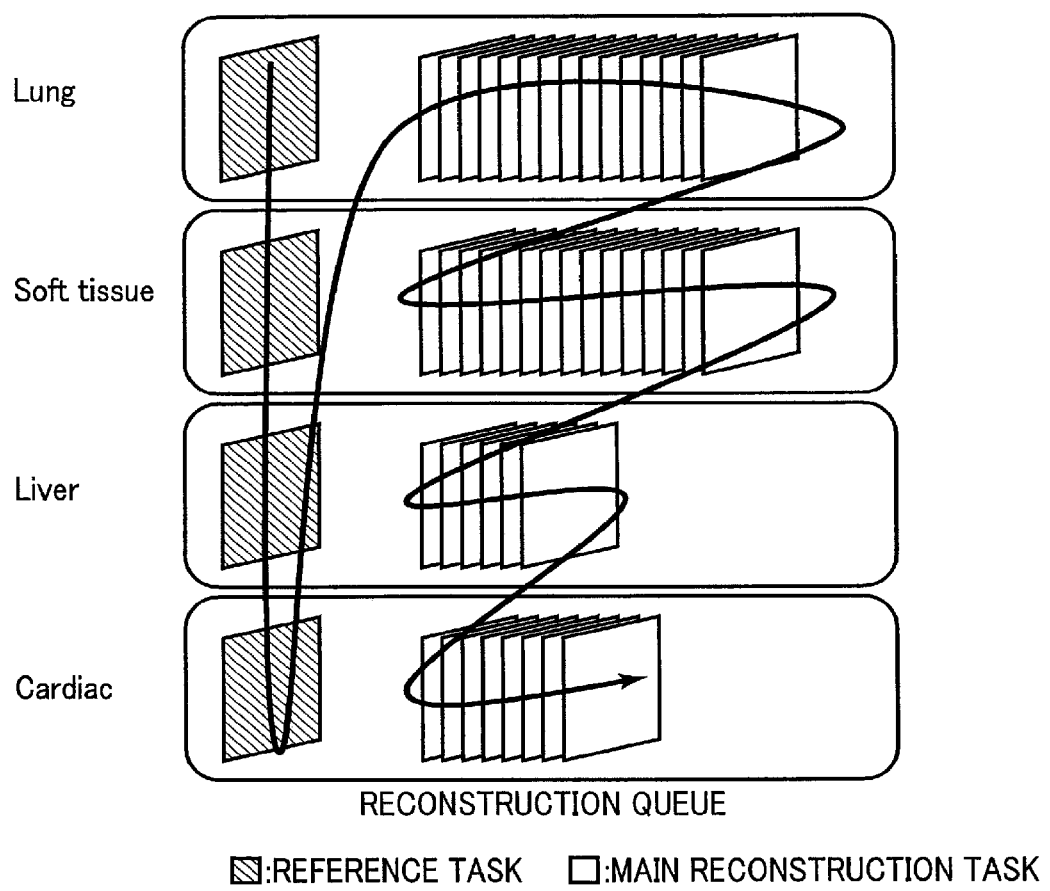
FIG. 7 is a view illustrating the order of reconstruction processes which are executed by the process illustrated in FIG. 5.

FIG. 7 is a view illustrating an example of the order of reconstruction processes which are executed by the process illustrated in FIG. 5. In FIG. 7, an arrow indicates the order of execution of the reconstruction processes. According to FIG. 7, it is understood that, by the process illustrated in FIG. 5, the reference tasks with small numbers of images are first executed, and then the main reconstruction tasks are executed.

As described above, in the present embodiment, if a reconstruction process is requested, the processing circuitry 35 generates, based on the request, a reference task in which a range of execution of the reconstruction process is limited, and a main reconstruction task in which the reconstruction process is executed for the other range. The processing circuitry 35 adds the reference tasks to the reconstruction queue, with a higher priority than the main reconstruction tasks. Then, the processing circuitry 35 executes the reference tasks which are accumulated in the reconstruction queue, earlier than the main reconstruction tasks. Thereby, the outline of each reconstruction image can be confirmed without waiting for the execution of preceding reconstruction processes. Thus, compared to the case of successively executing reconstruction processes, since the reconstruction images generated in the reference tasks can first be confirmed, an error of the condition setting, re-execution of imaging, etc. can be judged without waiting for the execution of the entire reconstruction process.

According to the X-ray CT apparatus 1 of the present embodiment, the requested reconstruction process can efficiently be executed. In addition, before the main reconstruction task is executed, the main reconstruction task can be canceled or the reconstruction process can be re-set. Therefore, the reconstruction process function 356 can efficiently be operated, and the through-put of the entirety of the examination is enhanced, leading to an improvement of the work flow.

Furthermore, since the reference tasks are executed prior to the main reconstruction tasks, at least one reconstruction image is generated prior to the execution of the main reconstruction task in each of requested reconstruction processes. Specifically, if the reference tasks are completed, it can be confirmed whether all images necessary for the examination are queued or not, and a survey of the entirety of the examination can be made. In other words, without waiting for the execution of the entirety of the reconstruction process, a list of images of the entire examination can be viewed, and the number of issued reconstruction requests, etc. can easily be understood. The reconstruction image, which is displayed after the completion of the reference task, may have the size of the generated image as such, or may be a reduced image reduced such as a thumbnail image.

Besides, if the reconstruction images are generated by the reference tasks, the processing circuitry 35 executes the following processes by utilizing the generated reconstruction images.

(Deletion of the Main Reconstruction Task from the Reconstruction Queue)

By the queue management function 355, the processing circuitry 35 judges whether the main reconstruction task accumulated in the reconstruction queue is to be deleted or not, in accordance with the good/poor state of the generated reconstruction image. Specifically, if the reference task is finished, a predetermined number of reconstruction images generated in the reference task are listed up in the image list. The user confirms the reconstruction images displayed on the image list. Note that the confirmation of reconstruction images by the user is not limited to the confirmation on the image list. The user may confirm reconstruction images displayed on a viewport for displaying the details of the reconstruction images.

The user judges whether the displayed reconstruction image is proper or not. If the user judges that the displayed reconstruction image is not proper, the user inputs, via the input interface 33, an instruction to delete the generated reconstruction image from the image list. That the reconstruction image is not proper means, for example, that the image quality is poor, such as when noise exists in the image, and that the position of the ROI is incorrect. That the reconstruction image is not proper may be, in other words, that the reconstruction condition is not proper. In accordance with an input from the user, the processing circuitry 35 deletes, by the display control function 358, the reconstruction image from the image list. If the reconstruction image is deleted from the image list, the processing circuitry 35 searches for the main reconstruction task corresponding to the deleted reconstruction image by the queue management function 355. Here, the term "corresponding" means, for example, that the reference task and the main reconstruction task are mutually associated. This may also mean that the reconstruction condition of the main reconstruction task and the reconstruction condition of the reference task are substantially identical. The processing circuitry 35 judges whether the main reconstruction task discovered by the search is being executed or not. When the discovered reconstruction task is being executed, the processing circuitry 35 stops the currently executed main reconstruction task, and then deletes this main reconstruction task from the reconstruction queue. When the discovered reconstruction task is not being executed, the processing circuitry 35 deletes the discovered main reconstruction task from the reconstruction queue.

Figure 8:
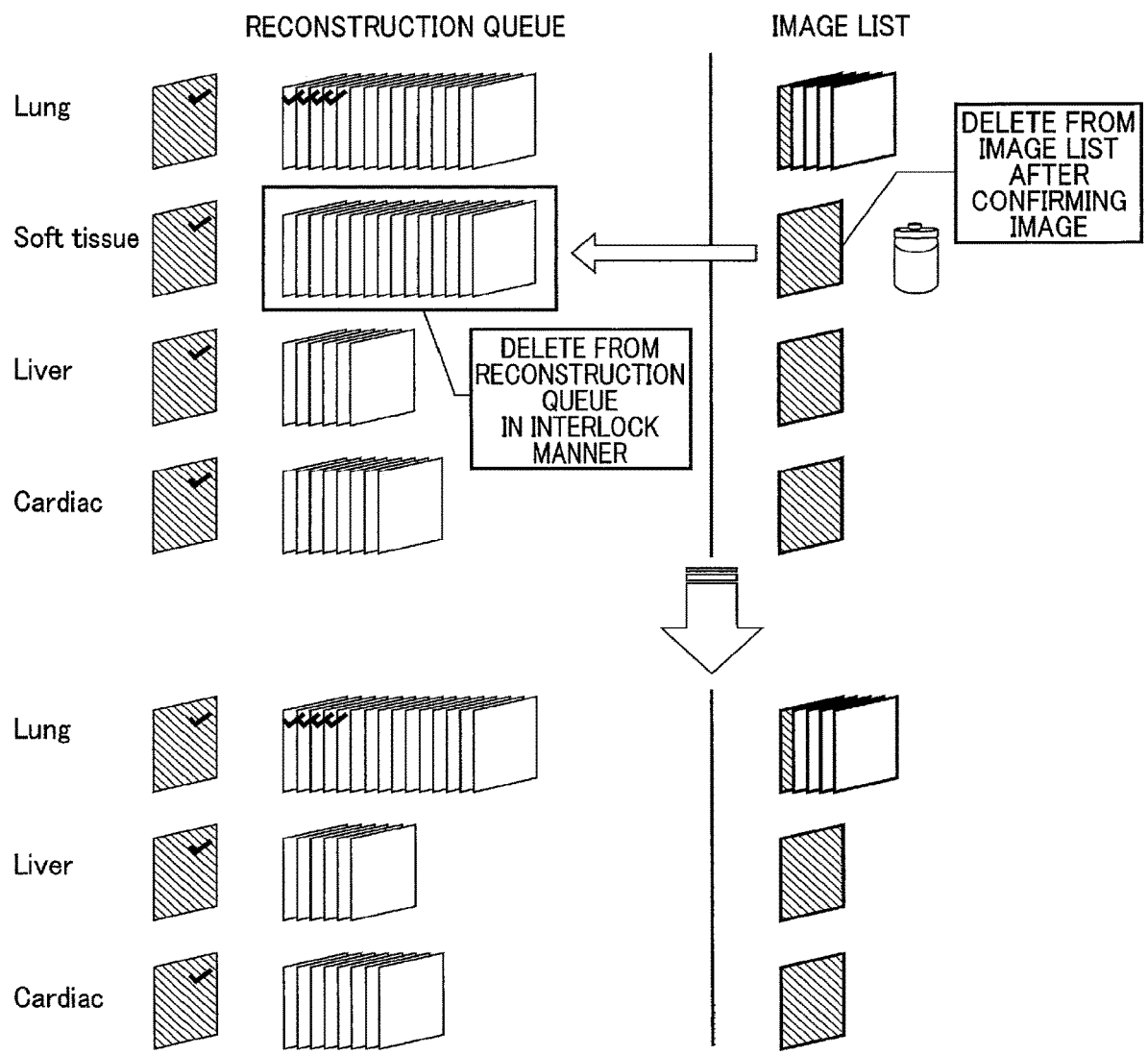
FIG. 8 is a view illustrating a process at a time when the processing circuitry shown in FIG. 1 deletes a main reconstruction task from the reconstruction queue.

FIG. 8 is a view illustrating an example of a process at a time when the processing circuitry shown in FIG. 1 deletes a main reconstruction task from the reconstruction queue. According to FIG. 8, while the reconstruction task of the lungs is being executed, an instruction is input from the user to delete reconstruction images generated for the soft tissue, which are displayed on the image list. If the instruction for deletion is input with respect to the reconstruction images of the soft tissue, the processing circuitry 35 deletes the reconstruction images of the soft tissue from the image list, and deletes the main reconstruction task of the soft tissue from the reconstruction queue. Thereby, the reconstruction task of the lungs, which is being executed, and the reconstruction tasks of the liver and heart, which are yet to be executed, are arranged in the reconstruction queue.

In this manner, in interlock with the deletion of the reconstruction image from the image list, the main reconstruction task corresponding to this reconstruction image is deleted from the reconstruction queue. Since the reconstruction image and the main reconstruction task are processed in an interlocking manner, the frequency of use of the queue list by the user decreases. Thus, the user can intuitively operate the tasks accumulated in the reconstruction queue. Furthermore, even if the concept of the queue is not understood, the operation can be performed based on the output data. Therefore, easy-to-understand operability can be provided, without depending on the worker's experience.

Note that the process of deleting the main reconstruction task from the reconstruction queue is not limited to the above-described process. For example, the reconstruction image generated by the execution of the reference task may not be displayed on the image list. Specifically, by the queue management function 355, the processing circuitry 35 acquires the information representative of the image quality such as image SD, based on the reconstruction image data generated by the execution of the reference task. When the information representative of the image quality fails to meet a preset condition, the processing circuitry 35 judges that the image quality of the reconstruction image is poor, i.e., the reconstruction image is not proper, and deletes the generated reconstruction image data and searches for the main reconstruction task corresponding to the deleted reconstruction image data. The processing circuitry 35 judges whether the main reconstruction task discovered by the search is being executed or not. When the discovered main reconstruction task is being executed, the processing circuitry 35 stops the currently executed main reconstruction task, and then deletes this main reconstruction task from the reconstruction queue. When the discovered main reconstruction task is not being executed, the processing circuitry 35 deletes the discovered main reconstruction task from the reconstruction queue.

(Change of the Order of Main Reconstruction Tasks in the Reconstruction Queue)

The processing circuitry 35 changes, by the queue management function 355, the order of main reconstruction tasks accumulated in the reconstruction queue, in accordance with the user's action on the generated reconstruction image. Specifically, if all reference tasks are finished, a predetermined number of reconstruction images generated in each reference task are listed up on the image list. The user inputs, via the input interface 33, an instruction to select any one of the reconstruction images which are displayed, for example, in parallel, on the image list. The instruction to select any one of the displayed reconstruction images includes, for example, an instruction to display any one of the displayed reconstruction images on a viewport. The instruction to display the reconstruction image on the viewport may also be realized by an action of dragging the reconstruction image displayed on the image list, and dropping the reconstruction image on a viewport area.

If any one of the displayed reconstruction images is selected, the processing circuitry 35 searches for the main reconstruction task corresponding to the selected reconstruction image by the queue management function 355. The processing circuitry 35 judges whether the main reconstruction task discovered by the search is being executed or not. When the discovered main reconstruction task is being executed, the processing circuitry 35 keeps the state as such. When the discovered main reconstruction task is not being executed, the processing circuitry 35 stops the currently executed main reconstruction task, and then moves the discovered main reconstruction task to the top of the reconstruction queue.

Figure 9:
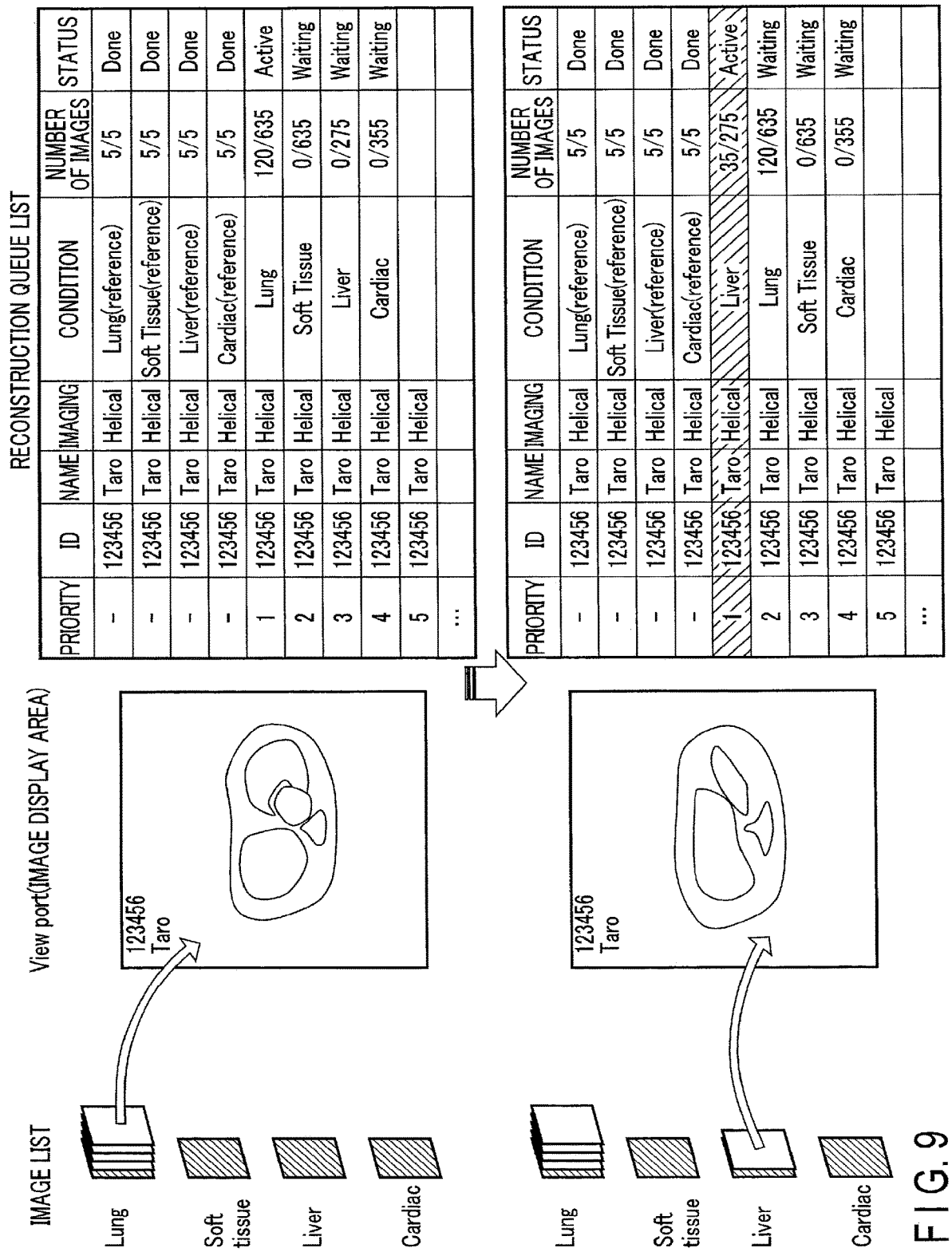
FIG. 9 is a view illustrating a process at a time when the processing circuitry shown in FIG. 1 changes the order of main reconstruction tasks in the reconstruction queue.

FIG. 9 is a schematic view illustrating an example of a process at a time when the processing circuitry 35 shown in FIG. 1 changes the order of main reconstruction tasks in the reconstruction queue. According to FIG. 9, when the reconstruction image of the lungs is displayed on the viewport, the execution of the main reconstruction task of the lungs is continued. On the other hand, when the reconstruction image of the liver is displayed on the viewport, the main reconstruction task of the lungs is suspended, and the main reconstruction task of the liver is moved to the top of the reconstruction queue, so that the main reconstruction task of the liver is executed with priority.

In this manner, if the reconstruction image displayed on the image list is selected, the priority of the corresponding main reconstruction task is raised. Thus, the user can intuitively operate the tasks accumulated in the reconstruction queue.

Figure 10:
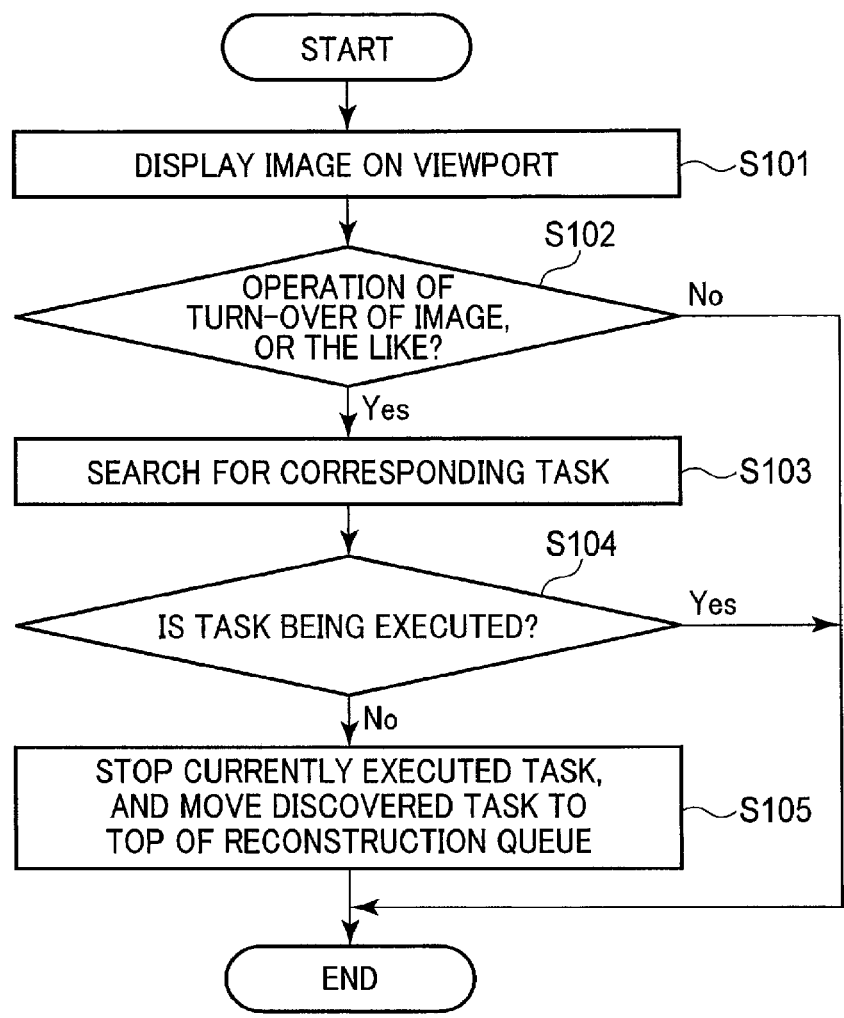
FIG. 10 is a flowchart illustrating a process at a time when the processing circuitry shown in FIG. 1 changes the order of main reconstruction tasks in the reconstruction queue.

Note that the selection of the reconstruction image displayed on the image list is not limited to the above. For example, when a predetermined action is performed on the reconstruction image displayed on the viewport, the reconstruction image may be treated as having being selected. The action on the reconstruction image displayed on the viewport includes, for example, an action such as turning-over of the reconstruction image displayed on the viewport. FIG. 10 is a flowchart illustrating an example of a process at a time when the processing circuitry shown in FIG. 1 changes the order of main reconstruction tasks in the reconstruction queue in accordance with an action on a reconstruction image displayed on the viewport.

If the processing circuitry 35 accepts an instruction to display a reconstruction image on the viewport, the processing circuitry 35 displays the reconstruction image on the viewport by the display control function 358 (step S101). The processing circuitry 35 judges whether an action such as turning-over of the reconstruction image displayed on the viewport is given by the user (step S102). If a predetermined action is given by the user on the reconstruction image displayed on the viewport (Yes in step S102), the processing circuitry 35 searches for the main reconstruction task corresponding to the selected reconstruction image by the queue management function 355 (step S103). On the other hand, if no action is given by the user on the main reconstruction image displayed on the viewport (No in step S102), the processing circuitry 35 terminates the process.

The processing circuitry 35 judges whether the main reconstruction task discovered by the search is being executed or not (step S104). When the discovered main reconstruction task is being executed (Yes in step S104), the processing circuitry 35 terminates the process. On the other hand, when the discovered main reconstruction task is not being executed (No in step S104), the processing circuitry 35 stops the currently executed main reconstruction task and then moves the discovered main reconstruction task to the top of the reconstruction queue (step S105).

In addition, when an instruction is input by the user to select any one of the reconstruction images displayed on the image list, the processing circuitry 35 may move the main reconstruction task having a high correlation to the selected reconstruction image to an upper position in the reconstruction queue. Specifically, if any one of the reconstruction images displayed on the image list is selected, the processing circuitry 35 searches for a first main reconstruction task corresponding to the selected reconstruction image by the queue management function 355, and searches for a second main reconstruction task having a high correlation to the first main reconstruction task. The processing circuitry 35 judges whether the correlation is high or not, for example, based on the degree of similarity between the reconstruction conditions. Alternatively, the processing circuitry 35 may judge whether the correlation is high or not, based on the relationship between specific parameters included in the reconstruction conditions of the reconstruction tasks. The relationship of specific parameters is registered in advance, for example, in a lookup table (LUT) or the like stored in the memory 31, and the processing circuitry 35 may preferably refer to the lookup table (LUT) or the like, when necessary. The processing circuitry 35 moves the first main reconstruction task discovered by the search to the top of the reconstruction queue, and moves the second main reconstruction task to an upper position of the reconstruction queue, for example, to the second position of the reconstruction queue. When the correlation between images is high, as in the case of reconstruction images acquired before and after contrast-enhanced photography, it is highly possible that the reconstruction images are treated as a pair by a clinical application and interpretation of radiogram. By expediting the execution of the main reconstruction task having a high correlation to the reconstruction image of interest, it becomes possible to quickly start the next action, such as the execution of a clinical application and the start of interpretation of radiogram.

The processing circuitry 35 may not search for the second main reconstruction task having the high correlation by the processing circuitry 35 itself. For example, the processing circuitry 35 is connected, via the communication interface 34, to an external analysis apparatus which executes a predetermined clinical application on the reconstruction images. In the case where the analysis apparatus requires two reconstruction images, for example, before and after contrast-enhanced photography, in order to execute the clinical application, if the analysis apparatus could receive only one of the reconstruction images, the analysis apparatus transmits a request signal for the other reconstruction image. If the processing circuitry 35 receives, by the queue management function 355, the request signal from the analysis apparatus, the processing circuitry 35 changes the order in the reconstruction queue of the main reconstruction task relating to the requested reconstruction image.

Figure 11:
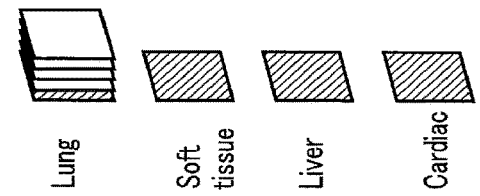
FIG. 11 is a view illustrating a process at a time when the processing circuitry shown in FIG. 1 changes the order of main reconstruction tasks in the reconstruction queue in accordance with a request from the outside.
Figure 11:
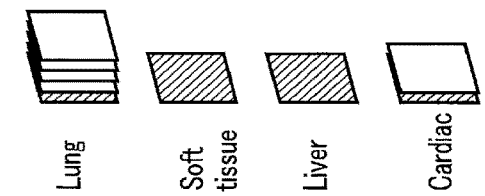

FIG. 11 is a schematic view illustrating an example of a process at a time when the processing circuitry shown in FIG. 1 changes the order of main reconstruction tasks in the reconstruction queue in accordance with a request from the outside. According to FIG. 11, a reconstruction image of the heart (Cardiac) is requested, for example, by an analysis apparatus existing on the outside. The processing circuitry 35 moves the requested main reconstruction task of the heart to the top of the reconstruction queue, and executes the main reconstruction task of the heart with priority.

(Transfer Setting and Protection Setting of Reconstruction Images)

In the system control function 351, the processing circuitry 35 executes transfer setting and protection setting on reconstruction images generated by the main reconstruction task. Specifically, if all reference tasks are finished, a predetermined number of reconstruction images generated by each reference task are listed up on the image list. The user confirms the reconstruction images displayed on the image list. If the reconstruction images are proper, the user inputs, via the input interface 33, a transfer request for the proper reconstruction images, regardless of whether the main reconstruction task is being executed or not. Each time the reconstruction image generated by the same main reconstruction task is added to the image list, the processing circuitry 35 adds a transfer flag to the added main reconstruction image. If the present main reconstruction task is finished, the processing circuitry 35 transfers batchwise the reconstruction images with the transfer flags to the destination of transmission.

In addition, the user confirms the reconstruction images displayed on the image list. If the reconstruction images are proper, the user inputs, via the input interface 33, a protection request for the proper reconstruction images, regardless of whether the main reconstruction task is being executed or not. Each time the reconstruction image generated by the same main reconstruction task is added to the image list, the processing circuitry 35 sets a protection flag to the added main reconstruction image. If the present main reconstruction task is finished, the processing circuitry 35 executes batchwise a protection process for the reconstruction images with the protection flags.

In this manner, by issuing the transfer request and protect request for the reconstruction images generated by the reference task, a post-process, such as the transfer process and protect process, is executed after the end of execution of the main reconstruction task. Thereby, the wait time for work can be reduced without executing a special object or an interlock.

(Display of the Status of Execution of the Main Reconstruction Task)

Figure 12:
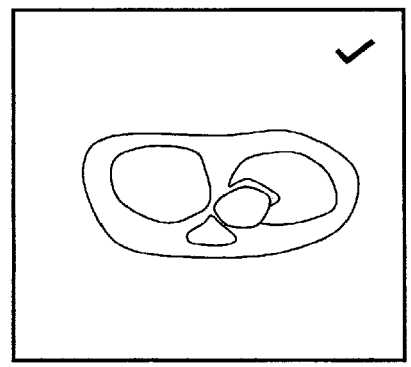
FIG. 12 is a view illustrating an icon of process completion, which is displayed on a reconstruction image of the lungs.
Figure 13:
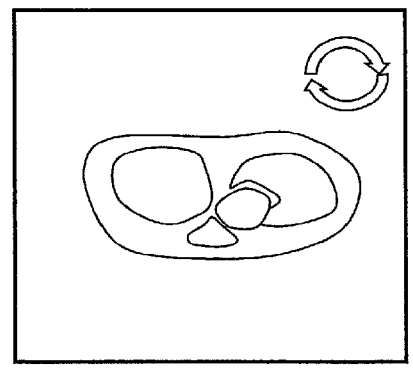
FIG. 13 is a view illustrating an icon of execution-in-progress, which is displayed on a reconstruction image of a soft tissue.
Figure 14:
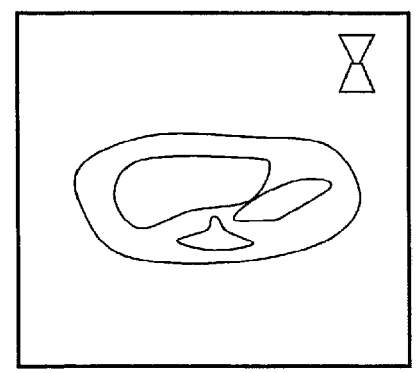
FIG. 14 is a view illustrating an icon of non-execution, which is displayed on a reconstruction image of the liver.

The processing circuitry 35 displays, by the display control function 358, information representative of the status of execution of the main reconstruction task, with respect to the reconstruction images generated by the reference task and displayed on the image list. Specifically, if all reference tasks are finished, the reconstruction images generated by each reference task are displayed on the image list. The processing circuitry 35 displays, on the reconstruction images generated by the reference tasks, icons indicating that the corresponding main reconstruction task is completed, is being executed, or is yet to be executed. FIG. 12 is a view illustrating an icon of process completion, which is displayed on the reconstruction image of the lungs. FIG. 13 is a view illustrating an icon of execution-in-progress, which is displayed on the reconstruction image of the soft tissue. FIG. 14 is a view illustrating an icon of non-execution, which is displayed on the reconstruction image of the liver.

Note that the information displayed on the reconstruction images is not limited to the icons. The information may be numerical values indicative of the status of execution of the main reconstruction task, an icon which varies in accordance with the status of execution, and the like.

OTHER EMBODIMENTS

In the first embodiment, by way of example, the case was described in which the reconstruction image generated by the reference task and the reconstruction image generated by the main reconstruction task are reconstructed by an identical image reconstruction method. However, the embodiment is not limited to this. As the image reconstruction method, there are methods which need much time in processing, such as iterative approximation reconstruction (IR) and metal artifact reduction (MAR). In addition, there is a method which needs data of a preset predetermined range when a reconstruction process is executed. When such methods are set in the reconstruction condition, much time is needed in creating reconstruction images, even in the case of the reference task in which the range of reconstruction processing is limited. Thus, in the task management function 354, the processing circuitry 35 generates a reference task of a different condition from the requested reconstruction condition, when it is estimated that a predetermined time or more is needed for the processing of the reference task.

Specifically, if imaging is completed, a request for the reconstruction process is input from the user via the input interface 33. If the request for the reconstruction process is input, the processing circuitry 35 reads out from the memory 31 a reconstruction condition associated with scanning, and generates a reconstruction task according to the reconstruction condition. If the reconstruction task is generated, the processing circuitry 35 reads out from the memory 31 the reconstruction condition of the generated reconstruction task by the task management function 354. The processing circuitry 35 judges whether preset methods, such as IR and MAR, are included in the read-out reconstruction condition. When the preset methods are included in the reconstruction condition, the processing circuitry 35 rewrites the reconstruction range of the reconstruction condition relating to the reconstruction task to a limited range, and rewrites the image reconstruction method to a method with a light load, for instance, a filtered backprojection method, thereby generating a reference task. In addition, the processing circuitry 35 generates a main reconstruction task having the same reconstruction condition as the reconstruction task. If the reference task and main reconstruction task are generated, the processing circuitry 35 adds, by the queue management function 355, the reference task and main reconstruction task to the reconstruction queue.

If the reference task is executed, a dummy image with reduced processing is provisionally added to the image list. In the main reconstruction task which is executed after the reference task, a reconstruction image according to the requested reconstruction method is generated from the beginning, and the generated reconstruction image is added to the image list. Then, if the main reconstruction task is finished, the dummy image is deleted from the image list.

FIG. 15 is a schematic view illustrating an example of a process in which the processing circuitry 35 shown in FIG. 1 adds a dummy image to the image list. According to FIG. 15, with respect to the soft tissue, a reference task in which the image reconstruction method was changed is accumulated in the reconstruction queue. The processing circuitry 35 generates a dummy image by executing the reference task of the soft tissue. The processing circuitry 35 distinguishes and manages the dummy image and the reconstruction images generated by executing the main reconstruction task. If the main reconstruction task is finished, the processing circuitry 35 deletes the dummy image.

Note that the reference task generated by the processing circuitry 35 may generate a preset substitute image. Thus, by the execution of the reference task, the dummy image as the substitute image is provisionally added to the image list.

By such setting as to generate the dummy image by the execution of the reference task, even when an image reconstruction method which consumes much time is set, the outline of each reconstruction image can be confirmed without waiting for the completion of the reconstruction process.

Besides, in the first embodiment, a concrete example is described in which a reconstruction process in a helical scan mode, for instance, is assumed, and the processing circuitry 35 in the task management function 354 generates the reference task by rewriting the reconstruction range of the reconstruction condition of the reconstruction task to a predetermined small range, and generates the main reconstruction task by rewriting the reconstruction range of the reconstruction condition of the reconstruction task to a range excluding the reconstruction range set in the reference task.

However, scan modes that can be set in the X-ray CT apparatus 1 of the first embodiment include an S & S (Step & Shoot) scan in which a conventional scan is executed multiple times while displacing the position. In such a scan mode, in one reconstruction task, a plurality of reconstruction sub-tasks, in which the ranges of execution of the reconstruction process are individually specified, are integrated and managed.

The processing circuitry 35 may switch the generation method of reference tasks and main reconstruction tasks in accordance with the scan mode. Specifically, the processing circuitry 35 generates a reference task by extracting, in the S & S scan, a part of the reconstruction conditions of the reconstruction tasks, for example, a part of reconstruction sub-tasks. In addition, the processing circuitry 35 generates a main reconstruction task, based on reconstruction conditions from which the part of the conditions is extracted, for example, based on the other reconstruction sub-tasks.

To be more specific, for example, as regards the S & S scan of the thoracoabdominal region, the processing circuitry 35 extracts a reconstruction sub-task which includes, as a reconstruction range, several mm from the beginning of the target range of S & S scan, or several mm from the position where a predetermined internal organ is included. Based on the extracted reconstruction sub-task, the processing circuitry 35 generates a reference task relating to a predetermined internal organ. In addition, based on the remaining reconstruction sub-tasks from which the reconstruction sub-task is extracted, a main reconstruction task relating to the predetermined internal organ is generated.

Besides, in the first embodiment, the operation of the X-ray CT apparatus 1 was described by way of example. However, the embodiment is not limited to this. The reconstruction process may be executed in an image generation apparatus 2.

Figure 16:
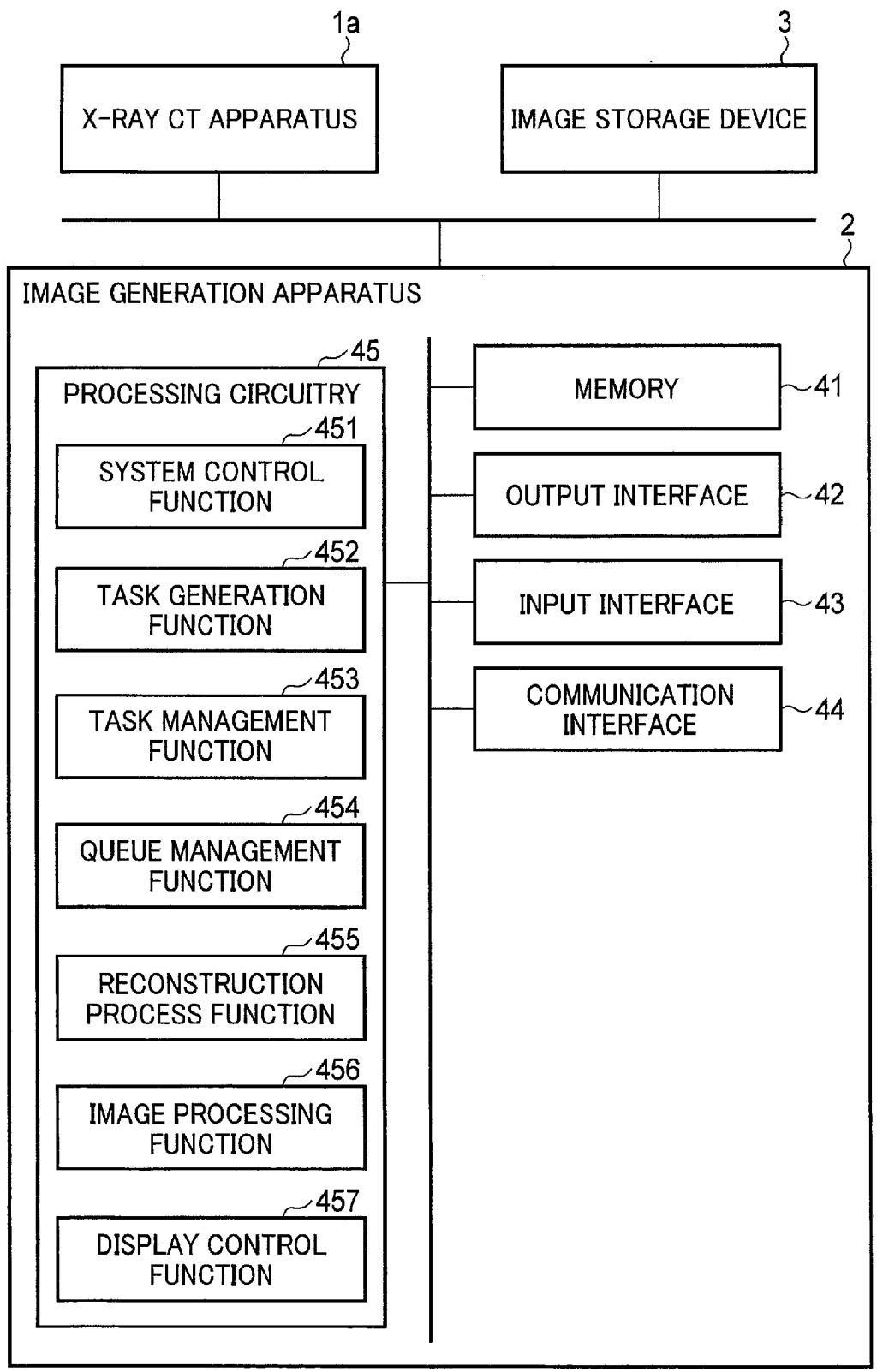
FIG. 16 is a view illustrating a medical information system including an image generation apparatus according to another embodiment.

FIG. 16 is a view illustrating an example of a medical information system including the image generation apparatus 2 according to another embodiment. The medical information system illustrated in FIG. 16 includes an X-ray CT apparatus 1a, the image generation apparatus 2, and an image storage apparatus 3. The X-ray CT apparatus 1a, image generation apparatus 2 and image storage apparatus 3 are directly or indirectly connected so as to be mutually communicable by, for example, an intra-hospital LAN (Local Area Network) installed in a hospital.

The X-ray CT apparatus 1a is an apparatus which generates projection data by imaging a subject. If a request for a reconstruction process is input from the user, the X-ray CT apparatus 1a transmits projection data and a request signal for the reconstruction process to the image generation apparatus 2.

The image generation apparatus 2 is an apparatus which applies an image reconstruction process on the projection data generated by the X-ray CT apparatus 1a. The image generation apparatus 2 illustrated in FIG. 16 includes a memory 41, an output interface 42, an input interface 43, a communication interface 44 and processing circuitry 45.

The processing circuitry 45 is a processor which controls the operation of the entirety of the image generation apparatus 2. The processing circuitry 45 executes a program stored in the memory 41, thereby realizing a function corresponding to the executed program. For example, the processing circuitry 45 executes a system control function 451, a task generation function 452, a task management function 453, a queue management function 454, a reconstruction process function 455, an image processing function 456, and a display control function 457. The system control function 451, task generation function 452, task management function 453, queue management function 454, reconstruction process function 455, image processing function 456 and display control function 457 execute the same processes as the system control function 351, task generation function 353, task management function 354, queue management function 355, reconstruction process function 356, image processing function 357 and display control function 358 according to the first embodiment.

Note that the processing circuitry 45 may include, or may not include, the task generation function 452 and task management function 453. In this case, the X-ray CT apparatus 1a includes the task generation function and task management function. The processing circuitry 45 receives information relating to the reference task and information relating to the main reconstruction task, which is transmitted from the X-ray CT apparatus 1a. The processing circuitry 45 adds, by the queue management function 454, the reference task and main reconstruction task to the reconstruction queue.

In the above embodiments, by way of example, the case was described in which if the reconstruction process is requested, the reconstruction task is generated by the task generation function 353, 452, and the reference task and main reconstruction task are generated by the task management function 354, 453, based on the reconstruction task. However, the embodiments are not limited to this. In the task management function 354, 453, the reference task and main reconstruction task may be generated in accordance with a request for the reconstruction process.

The term "processor" used in the description of the embodiments means, for example, a CPU (central processing unit), a GPU (Graphics Processing Unit), or circuitry such as an ASIC (Application Specific Integrated Circuit) or a programmable logic device (e.g. SPLD (Simple Programmable Logic Device), CPLD (Complex Programmable Logic Device), FPGA (Field Programmable Gate Array)). The processor realizes the functions by reading and executing programs stored in storage circuitry. Note that, instead of storing programs in the storage circuitry, such a configuration may be adopted that the programs are directly assembled in the circuitry of the processor. In this case, the processor realizes the functions by reading and executing programs assembled in the circuitry of the processor. Note that the embodiments are not limited to the case in which each processor is composed as single circuitry. Each processor may be composed by combining a plurality of independent circuitry elements, thereby realizing the functions. Furthermore, a plurality of constituent elements in each embodiment may be integrated into a single processor, thereby realizing the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
processing circuitry configured to, for each of a plurality of reconstruction requests:

receive as one of the plurality of reconstruction requests a single reconstruction request for image reconstruction using a projection data set acquired by a scan including radiation and detection of X-rays, the single reconstruction request being a single request to reconstruct a series of images of one of examination target parts of a subject;

divide the single request to reconstruct the series of image into a respective pair of tasks including (1) a respective first task for reconstructing at a first priority level a first set of images in a first reconstruction range of the series of images and (2) a respective second task for reconstructing at a second priority level a second set of images in a second reconstruction range of the series of images, wherein a number of images in the first set of images is smaller than a number of images in the second set of images, and wherein the first priority level is a higher priority level than the second priority level;

manage, as a priority queue, an order of execution of the respective first task and the respective second task by adding the respective first task and the respective second task to the priority queue such that all respective second tasks are scheduled to be executed after all respective first tasks, and execute all the respective first tasks before any of the second tasks.

2. The X-ray computed tomography apparatus according to claim 1, wherein the processing circuitry is configured to cause a display to display a plurality of images reconstructed by execution of the respective first tasks of the plurality of reconstruction requests.

3. The X-ray computed tomography apparatus according to claim 1, wherein the second reconstruction range is different from the first reconstruction range.

4. The X-ray computed tomography apparatus according to claim 1, wherein the second reconstruction range includes a part of the first reconstruction range.

5. The X-ray computed tomography apparatus according to claim 1, wherein the first reconstruction range and the second reconstruction range are identical or different for each of the plurality of reconstruction requests.

6. The X-ray computed tomography apparatus according to claim 1, wherein for at least one of the plurality of reconstruction requests, the processing circuitry configured to divide the single request comprises circuitry configured to generate the respective first task to have a reduced load when reconstructing the first reconstruction range as compared to when the second task reconstructs the first reconstruction range as part of reconstructing the second reconstruction range.

7. The X-ray computed tomography apparatus according to claim 2, wherein the processing circuitry is configured to cause the display to display the plurality of images reconstructed by the execution of the respective first tasks, before an end of execution of any of the respective second tasks in the priority queue.

8. The X-ray computed tomography apparatus according to claim 2, wherein the processing circuitry is configured so that in response to an input of an instruction for deleting a to-be-deleted image of the plurality of images that are displayed, the processing circuitry deletes the respective second task paired with the respective first task used to generate the one the to-be-deleted image.

9. The X-ray computed tomography apparatus according to claim 1, wherein the processing circuitry is configured so that if an image quality of image data generated by execution of one of the respective first tasks fails to meet a preset condition, the processing circuitry deletes the image data failing to meet the preset condition and deletes the respective second task paired with the respective first task that generated the deleted image data.

10. The X-ray computed tomography apparatus according to claim 2, wherein the processing circuitry is configured so that in response to an input of an instruction for selecting one of the plurality of images, the processing circuitry reorders the priority queue such that the second set of images of the respective second task paired with the respective first task that generated the selected one of the plurality of images is set to be executed sooner than before the reordering.

11. The X-ray computed tomography apparatus according to claim 2, wherein the processing circuitry is configured so that in response to an input of an instruction for selecting one of the plurality of images, the processing circuitry places a priority on one of the respective second tasks which has a correlation to the selected one of the plurality of images over remaining another respective second task in the priority queue.

12. The X-ray computed tomography apparatus according to claim 2, wherein the processing circuitry is configured so that in response to an input of a transfer request for transferring one of the plurality of images, the processing circuitry transfers, upon execution of one or more of the second tasks which correspond to said one or more images to be transferred, image data generated by execution of said one or more second tasks, or both image data generated by execution of said one or more second tasks and image data of said one or more images to be transferred.

13. The X-ray computed tomography apparatus according to claim 2, wherein the processing circuitry is configured so that in response to an input of a protection request for protecting one of the plurality of images, the processing circuitry protects, upon execution of one or more of the second tasks which correspond to said one or more images to be protected, image data generated by execution of said one or more second tasks, or both image data generated by execution of said one or more second tasks and image data of said one or more images to be protected.

14. The X-ray computed tomography apparatus according to claim 2, wherein the processing circuitry is configured to display information indicative of a status of execution of a pending second task of the respective second tasks in association with a displayed image of the plurality of images generated by the respective first task paired with the pending second task.

15. The X-ray computed tomography apparatus according to claim 1, wherein, with respect to a respective pair of tasks, a first amount of data to be processed by the respective first task is less than a second amount of data to be processed by the respective second task.

16. The x-ray computed tomography apparatus according to claim 1, wherein, with respect to a respective pair of tasks, a load of a reconstruction process of the respective first task is lighter than a load of a reconstruction process of the respective second task, and the processing circuitry separately manages a first image generated by the respective first task and a second image generated by the respective second task.

17. An image generation apparatus comprising:
processing circuitry configured to, for each of a plurality of reconstruction requests:
receive as one of the plurality of reconstruction requests a single reconstruction request for image reconstruction using a projection data set acquired by a scan including radiation and detection of X-rays, the single reconstruction request being a single request to reconstruct a series of images of one of examination target parts of a subject;

divide the single request to reconstruct the series of image into a respective pair of tasks including (1) a respective first task for reconstructing at a first priority level a first set of images in a first reconstruction range of the series of images and (2) a respective second task for reconstructing at a second priority level a second set of images in a second reconstruction range of the series of images, wherein a number of images in the first set of images is smaller than a number of images in the second set of images, and wherein the first priority level is a higher priority level than the second priority level;

manage, as a priority queue, an order of execution of the respective first task and the respective second task by adding the respective first task and the respective second task to the priority queue such that all respective second tasks are scheduled to be executed after all respective first tasks, and execute all the respective first tasks before any of the second tasks.

18. The image generation apparatus according to claim 17, wherein the processing circuitry is configured to cause a display to display a plurality of images reconstructed by execution of the respective first tasks of the plurality of reconstruction requests.

19. A task management method comprising:

receiving a plurality of reconstruction requests, and for each of a plurality of reconstruction requests performing:

receiving as one of the plurality of reconstruction requests a single reconstruction request for image reconstruction using a projection data set acquired by a scan including radiation and detection of X-rays, the single reconstruction request being a single request to reconstruct a series of images of one of examination target parts of a subject;

dividing the single request to reconstruct the series of image into a respective pair of tasks including (1) a respective first task for reconstructing at a first priority level a first set of images in a first reconstruction range of the series of images and (2) a respective second task for reconstructing at a second priority level a second set of images in a second reconstruction range of the series of images, wherein a number of images in the first set of images is smaller than a number of images in the second set of images, and wherein the first priority level is a higher priority level than the second priority level;

managing, as a priority queue, an order of execution of the respective first task and the respective second task by adding the respective first task and the respective second task to the priority queue such that all respective second tasks are scheduled to be executed after all respective first tasks, and executing all the respective first tasks before any of the second tasks.

20. The task management method according to claim 19, further comprising causing a display to display a plurality of images reconstructed by execution of the respective first tasks of the plurality of reconstruction requests.

* * * * *